United States Patent [19]
Atherton et al.

[11] Patent Number: 5,821,747
[45] Date of Patent: Oct. 13, 1998

[54] METHOD AND APPARATUS FOR SCANNING A PLURALITY OF PARALLEL PIPES FOR FLAWS USING TUBE-TO-TUBE THROUGH TRANSMISSIONS

[75] Inventors: David L. Atherton, Kingston; Ad Shatat, Edmonton, both of Canada

[73] Assignee: Queen's University at Kingston, Kingston, Canada

[21] Appl. No.: 780,559

[22] Filed: Jan. 8, 1997

[51] Int. Cl.⁶ .................................................. G01N 27/90
[52] U.S. Cl. ........................ 324/220; 165/11.2; 324/240; 324/242
[58] Field of Search .................... 324/219–221, 324/240–242, 372; 165/11.1, 11.2; 376/249

[56] References Cited

U.S. PATENT DOCUMENTS

| | | | |
|---|---|---|---|
| 2,065,118 | 12/1936 | Davis, Jr. | ................................. 324/241 |
| 3,693,075 | 9/1972 | Förster | ................................. 324/220 X |
| 3,906,358 | 9/1975 | Stone | ................................. 324/220 |
| 4,901,023 | 2/1990 | Vail, III | ................................. 324/372 X |
| 5,124,641 | 6/1992 | Netter et al. | ......................... 324/219 X |
| 5,140,264 | 8/1992 | Metala et al. | ............................ 324/219 |

FOREIGN PATENT DOCUMENTS 150349  11/1981  Japan ..................................... 324/220

Primary Examiner—Gerard R. Strecker
Attorney, Agent, or Firm—Richard J. Hicks

[57] ABSTRACT

A method and apparatus for determining position size and shape of defects in a bundle of heat exchanger tubes are described. An AC current exciter coil is placed in one tube and a detector coil is placed in an adjacent tube. This configuration of exciter and detector coils reduces the blind spot effect caused by interference by tube support plates and allows the inspection multiple or finned heat exchanger tubing.

16 Claims, 9 Drawing Sheets

METHOD AND APPARATUS FOR SCANNING A PLURALITY OF PARALLEL PIPES FOR FLAWS USING TUBE-TO-TUBE THROUGH TRANSMISSIONS

FIELD OF THE INVENTION

This invention relates to remote field eddy current methods and apparatus for detecting flaws in bundles of small diameter pipes.

BACKGROUND OF INVENTION

Remote field eddy current (RFEC) methods for detecting flaws or anomalies in the walls of pipes or tubes are well known in the art. Conventionally, this through-wall method comprises inserting an exciter coil and a receiving or detecting coil into the pipe to be inspected and passing the coils axially along the tube. The exciter and detecting coils are axially displaced by about 2–3 outer diameters of the pipe. A low frequency AC current is passed through the exciter coil and the AC magnetic field, after transiting the wall twice, is measured by the detecting coil. Anomalies in the field generated are indicative of the location in the pipe of any flaws in the pipe wall. However, defects are normally measured twice and these two measurements can interface and thus complicate analysis. The probe is relatively long and difficult to maneuver around bends in the pipe being inspected and blind spots can occur in the vicinity of pipe support plates and the like. Blind spot reduction, but not elimination, may be achieved using one or more additional exciter coils but this compounds the maneuverability problem. Another disadvantage of the simple single detector RFEC method is that there is no elution of defects in the circumferential direction, i.e. it is not possible to distinguish between one deep defect or several less deep defects. Multiple detectors or scanning detectors are both used.

Another flaw detection method in pipes is known as the conventional eddy current (CEC) method. CEC is similar to RFEC except that the exciter and detector coils are closely spaced, and in some cases the detector coil may be omitted so that the exciter coil is used to measure its own field as a so-called reflected impedance probe. CEC is, however, problematic with ferromagnetic pipes, in which outer wall metal loss is very difficult to detect.

Improved methods for detecting flaws in pipes, such as bundles of small diameter heat exchanger tubes, which significantly decrease the "blind spot" effect and which use a relatively short probe would afford considerable economic benefit.

OBJECT OF INVENTION

One object of this invention is to provide a novel method for performing through wall eddy current measurements on a plurality (at least two) of relatively small diameter tubes so as to determine the size and location of flaws therein.

Another object of this invention is to provide an apparatus for eddy current flaw detection in a plurality of tubes.

BRIEF STATEMENT OF INVENTION

By one aspect of this invention, there is provided a method for detecting flaws in at least one of a plurality of metal pipes comprising: introducing an exciter coil into a first said metal pipe; introducing a detector coil into a second said metal pipe adjacent to said first metal pipe; energizing said exciter coil with an AC current; detecting an AC magnetic field generated by said AC current with said detector coil in said second pipe and an output signal therefrom; and determining size, shape and location of defects in said pipes by observing anomalies in said output signal.

By another aspect of this invention, there is provided an apparatus for detecting flaws in at last one of a plurality of spaced metallic pipes comprising: an AC exciter coil adapted for insertion into a first said metallic pipe; an AC magnetic field detector coil adapted for insertion into a second, adjacent or near, said metallic pipe; means to supply an AC current to said exciter coil so as to generate an AC magnetic field adjacent to said detector coil; means to observe an output signal from said detector coil; and means to determine size, shape and location of said flaws from anomalies in said output signal.

DETAILED DESCRIPTION OF PREFERRED EMBODIMENTS

Heat exchangers, as commonly used in the chemical and power industries, consist of bundles of parallel tubes or pipes contained within an outer shell. The pipes which may be either ferromagnetic or nonferromagnetic, are used to separate two heat exchanging thermodynamic fluids and generally have a relatively small (up to about 50 mm) outer diameter and relatively thin walls. To prevent sagging, the tubes are supported at intervals by vertical support plates.

Heat exchanger tubes are extremely prone to corrosion, partly due to the nature of the thermodynamic fluids, particularly liquids, passing through and partly due to dissolved gases and elevated temperatures. There are, however, several other causes of heat exchanger failure including mechanical vibrations, induced by high velocity fluids, which can cause fretting or vibration wear at the support plate locations. It has been found that the fretting wear is dependent on the clearance between pipe and plate—the larger the air gap, the higher the wear rate. This means that once fretting starts, the wear rate will accelerate. It is, therefore, advantageous to monitor the tubes in a heat exchanger regularly so as to determine fretting as early as possible.

While there are several inspection techniques available, none of the prior art techniques, except pulsed ultrasonics, can be used to identify wall loss reliably beneath support plates. It is frequently necessary, therefore, to employ both an electromagnetic method and an ultrasonic method of inspection which is, of course, both expensive and time consuming. In addition, ultrasonic inspection is somewhat complicated in that a liquid coupling medium usually must be employed to transmit the ultrasound from the probe into the tube wall, and furthermore the inspection speed is extremely slow (typically an order of magnitude lower than electromagnetic methods).

The tube-to-tube through transmission (T4) technique of the present invention does not suffer as greatly from support plate interference and can be used to inspect heat exchanger tubes under the support plates. T4 inspection may be carried out in any set of multiple metallic tubes, which may even be ferromagnetic. The distance between the pipes does not have to be constant and can vary from job to job. Indeed, even within the same inspection run, variations in inter-pipe distance can be tolerated, as long as the variations are limited (to within about 10%). Ultimately, the inter-pipe distance is restricted by the minimum signal level detectable by the receiver. The minimum detectable signal level is in turn determined by the amount of noise in the system.

Figure 1:
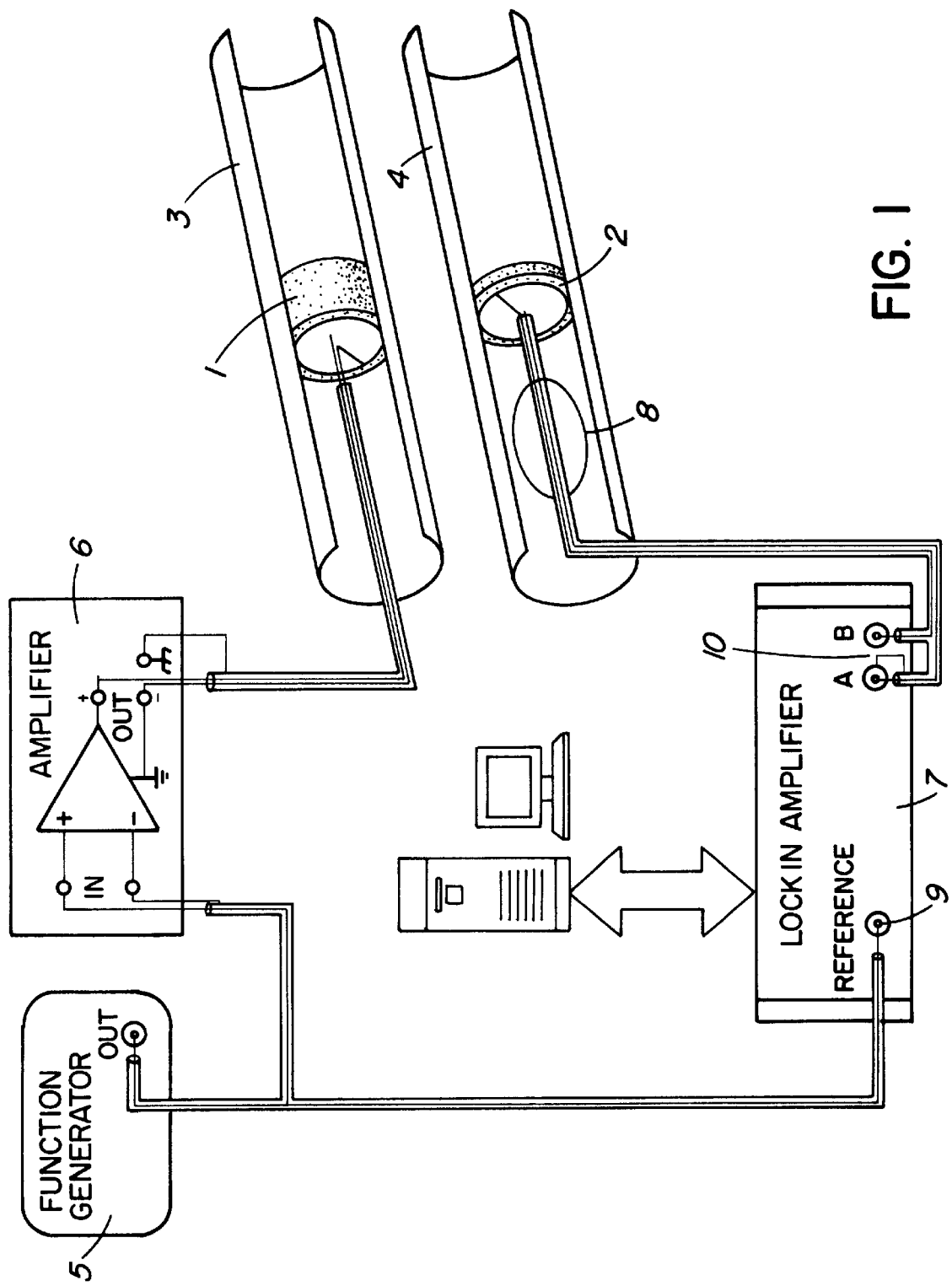
FIG. 1 is a sketch of a tube-to-tube through transmission (T4) apparatus according to one embodiment of the present invention.

In the simplest case, tube-to-tube transmission is used for the inspection of parallel pipes (for example in a heat exchanger). FIG. 1 shows an example of the basic configuration. In contrast to existing eddy current methods, transmitter 1 and receiver 2 are not located in the same pipe. Instead, transmitter 1 (exciter) and receiver 2 (detector) are aligned in different (usually neighbouring) pipes 3, 4. For convenience, FIG. 1 shows the exciter and detector oriented in the axial direction; this is not, however, essential. An array of radial detectors, for example, can have a much higher spatial resolution than the single axial detector. Similarly, the position and orientation of the exciter can be varied; the transmitter may be axially displaced from the receiver or even substituted by one or more radial transmitters. In addition, transmitter and receiver may be located in pipes, which are not direct neighbours. The arrangement of FIG. 1 is merely a preferred design; as long as transmitter and receiver are in different pipes, the configuration will basically be a tube-to-tube transmission arrangement.

The transmitting coil in FIG. 1 is driven by a low frequency signal, generated by a function generator 5. A bipolar power amplifier 6 may be placed between function generator 5 and transmitter 1 to improve signal strength. The output signal from the receiver 2 is fed to a lock-in amplifier or narrow bandwidth synchronous detector/amplifier 7 and, if desired, a preamplifier 8 can be used to make the detector signal less susceptible to noise pick up on the signal lines. The reference 9 for the lock-in amplifier 7 can be derived directly from the function generator or from the signal lines to the transmitter coil. The detector voltage is generally coupled to the differential input 10 of the lock-in amplifier 7 via a double wire (twisted) BNC cable.

Figure 2:
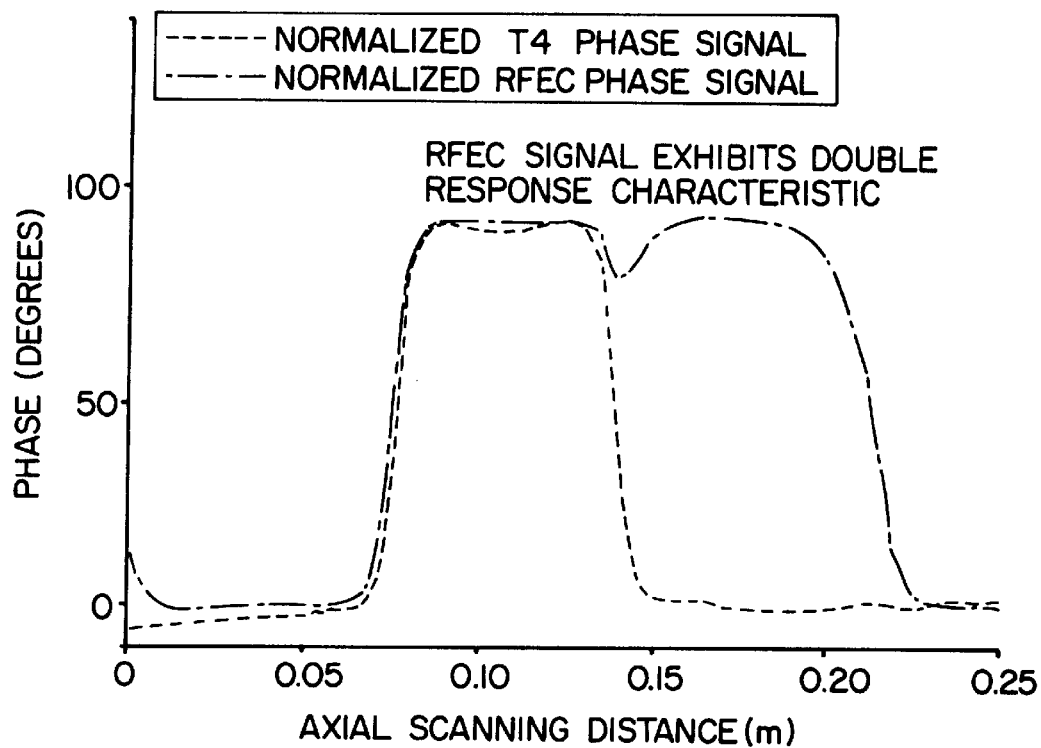
FIG. 2 is a phase strip chart or log plot for a full circumferential 50% deep, 55 mm wide exterior groove in a tube as determined by RFEC and T4 (I=300 mA@400 Hz).

When a pipe, containing flaws, is inspected using a tube-to-tube transmission probe, the flaws are registered only once for each probe traverse. This in contrast to remote field eddy current inspection, which registers the same defect twice: once when the detector passes the defect, and a second time when the exciter passes by. In FIG. 2, the same defect was inspected using an RFEC probe and a T4 probe. The transmitter of the T4 probe was located in clear pipe, while the receiver was used to scan the pipe with the defect. Except for the repetitive nature of the remote field eddy current response, the two signals seem to behave in a very similar way. The convenience of the single detection is clearly demonstrated by FIG. 2.

As mentioned in the introduction, electromagnetic inspection techniques have trouble sizing defects underneath support plates. The magnetic interference caused by the plates is such that measured signals are often difficult to analyse. As a consequence, the inspection company is not able to determine the state of the heat exchanger under the supports accurately.

Figure 3:
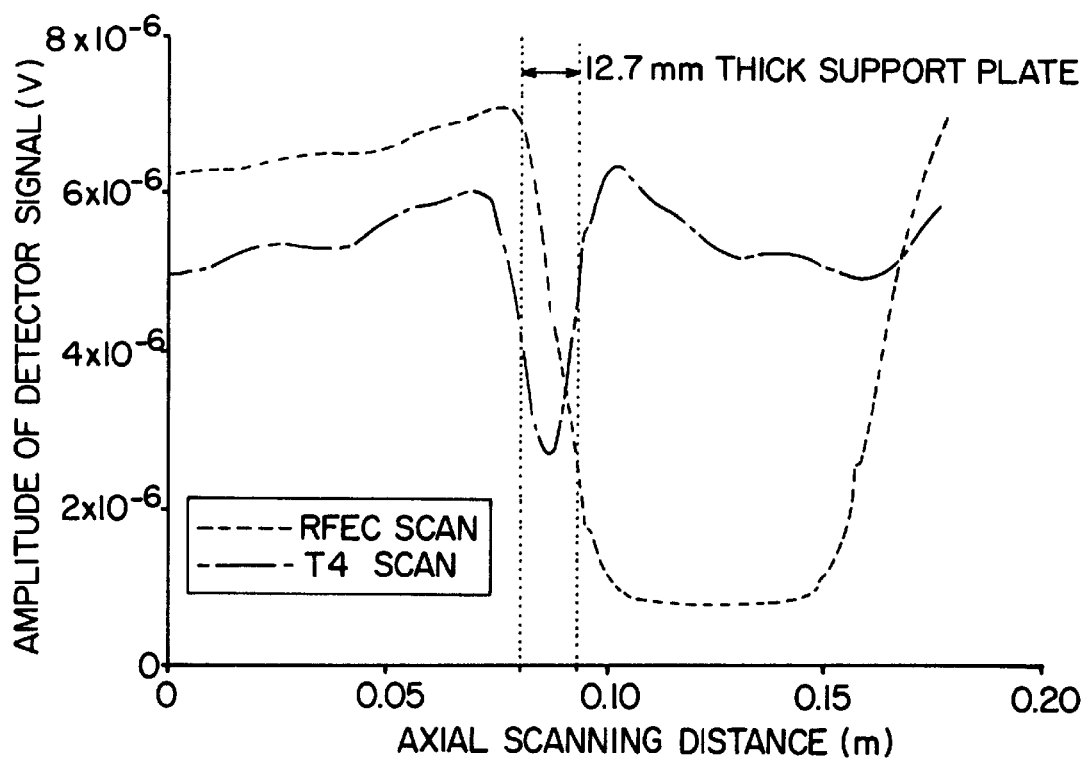
FIG. 3 is a phase strip chart for a 12.7 mm thick support plate as determined by RFEC and T4. Gap distance between pipe and plate is 0.2±0.05 mm (I=300 mA@205 Hz).

As previously noted, T4 suffers relatively little from the interference of support plates. This is partly because the energy flows in the radial direction (along the plate instead of perpendicular to it) and partly because the energy reaching the detector comes from two sides of the plate instead of one. FIG. 3 compares T4 inspection of a 12.7 mm thick plates with the corresponding RFEC scan. Not only is the T4 response small in amplitude, it also extends over a significantly shorter axial range.

In an alternative embodiment, the support plate response is displayed by combining the amplitude and phase response in a polar plot. This polar plot representation is referred to as the voltage plane display. To allow for comparison between different voltage plane plots, amplitude and phase are normalized (by normalizing the support plate signal to the full-wall signal) before calculating the corresponding in-phase (real) and quadrature (imaginary) components. Usually only the end point of the resulting complex phasor is plotted. Axial information on the position of the probe is obtained from the strip chart log plots. On the voltage plane display, a defect response will look like a trace starting at (1,0) and reaching out towards the skin depth spiral. Orientation and length of the trace give the operator information on the depth and extent of the defect. When the tube-to-tube support plate response of FIG. 3 is plotted using the voltage plane display, a characteristic signal is obtained (see FIG. 4).

Figure 4:
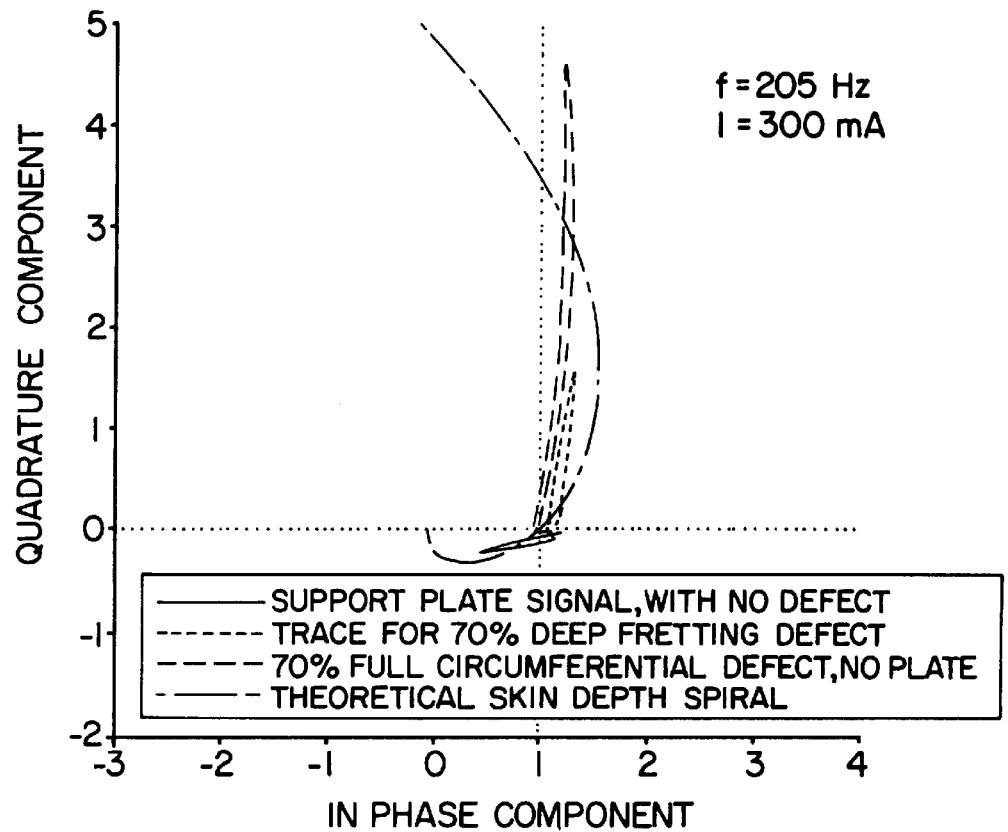
FIG. 4 is a graph illustrating tube-to-tube transmission plane polar plot responses for a 12.7 mm thick support plate, with and without groove simulating a 70% deep fretting defect. Groove in pipe with detector.

FIG. 4 also shows the voltage plane response of a 70% full circumferential defect. The trace starts at (1,0) and surpasses the theoretical skin depth spiral. When the defect is located underneath a support plate, the resulting voltage plane trace bears surprisingly little resemblance to the typical support plate response. Although the defect trace becomes significantly shorter, the trace is quite pointed and may be used for sizing purposes.

Figure 5:
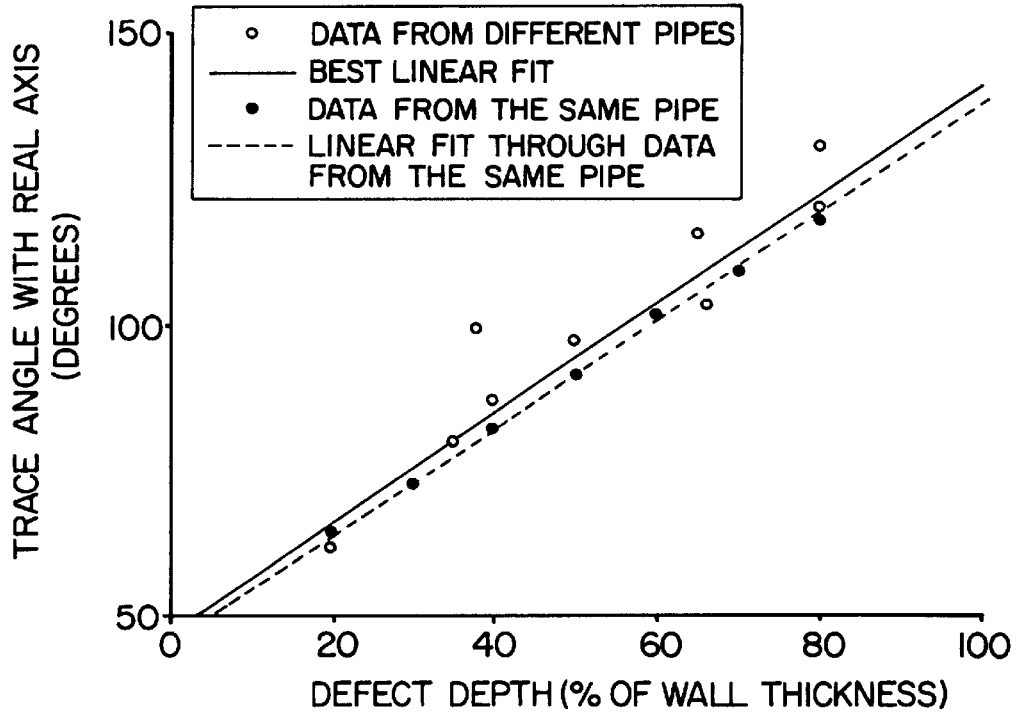
FIG. 5 is a graph illustrating the angle of T4 voltage plane traces versus defect depth for full circumferential, partial circumferential and flat bottom grooves. Frequency =310 Hz.

When no support plates are present, defects identified with the T4 method may be sized using the same procedures as employed for the RFEC technique. A popular depth sizing tool is the trace angle of the voltage plane display. The trace angle is defined as the angle between the voltage plane trace and the real axis. For T4, the trace angle is related to defect depth. FIG. 5 shows a depth sizing calibration curve for the trace angle.

An alternative way of determining the depth of full circumferential defects is by using multi-frequency analysis. Multi-frequency analysis is based on a skin depth equation, which approximates the behaviour of the T4 method as long as the remaining pipe wall thickness exceeds about one skin depth. According to the skin depth equation, the phase of the detector is linearly dependent on the square root of the frequency. The skin depth equation for the normalized detector signal is given by:

$$V_d = e^{\frac{t_c - t_d}{\delta}} e^{\frac{j(t_c - t_d)}{\delta}} \text{ with } \delta = \frac{1}{\sqrt{\pi f \sigma \mu}}$$

Where $t_c$ is the wall thickness of the clear pipe, and $t_d$ is the remaining wall thickness at the defect location. The difference, $t_c - t_d$, (the depth of the defect) is proportional to the phase of the normalized signal, which is obtained by dividing the defect response by the full wall signal. When the pipe has no wall loss, $t_d$ will equal $t_c$ and the resulting normalized signal will have a real component equal to one. The skin depth, $\delta$, is a function of the frequency (f), the permeability ($\mu$) and the conductivity ($\sigma$).

Figure 6:
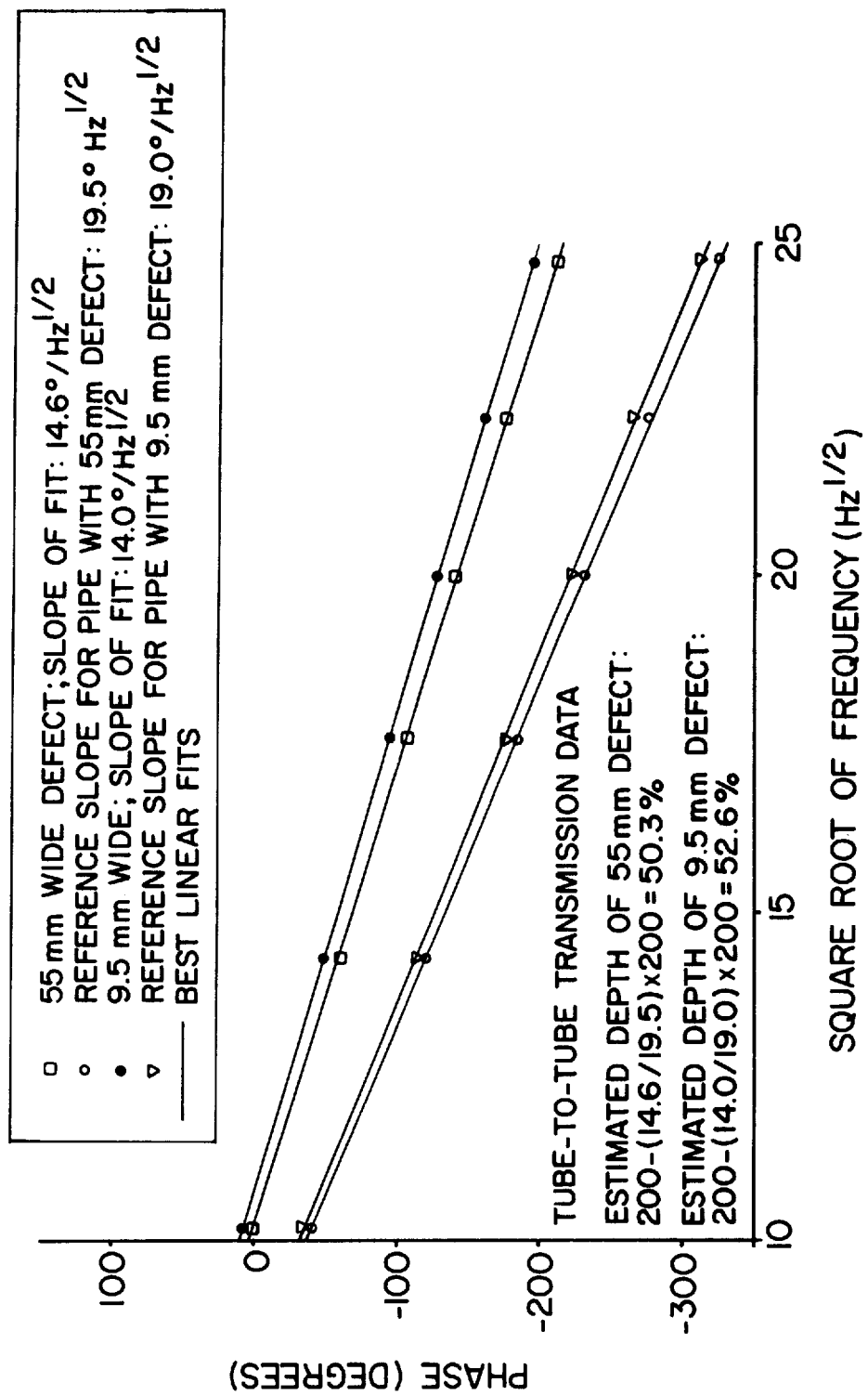
FIG. 6 is a graph illustrating defect depth sizing using a multi-frequency method. Two 50% deep full circumferential external groove defects with widths of 9.5 and 55 mm were located in the pipe with the detector.

According to equation 1, the slope of the linear graph between the phase and the square root of the frequency is proportional to the remaining wall thickness, and it can therefore be used to size the depth of the defect. To obtain the phase of the defect signal, the tip of the defect trace is followed on the voltage plane display. The phase at the maximum position of the trace is plotted versus the square root of the frequency. FIG. 6 shows the phase-frequency curves for two full circumferential grooves. Both grooves are 50% deep and located in the pipe with the receiver coil. Their axial lengths, however, are different: 9.5 mm and 55 mm. Using the slopes of the curves in combination with the basic skin depth relationship the grooves can be estimated as 50% and 53% deep.

Figure 7:
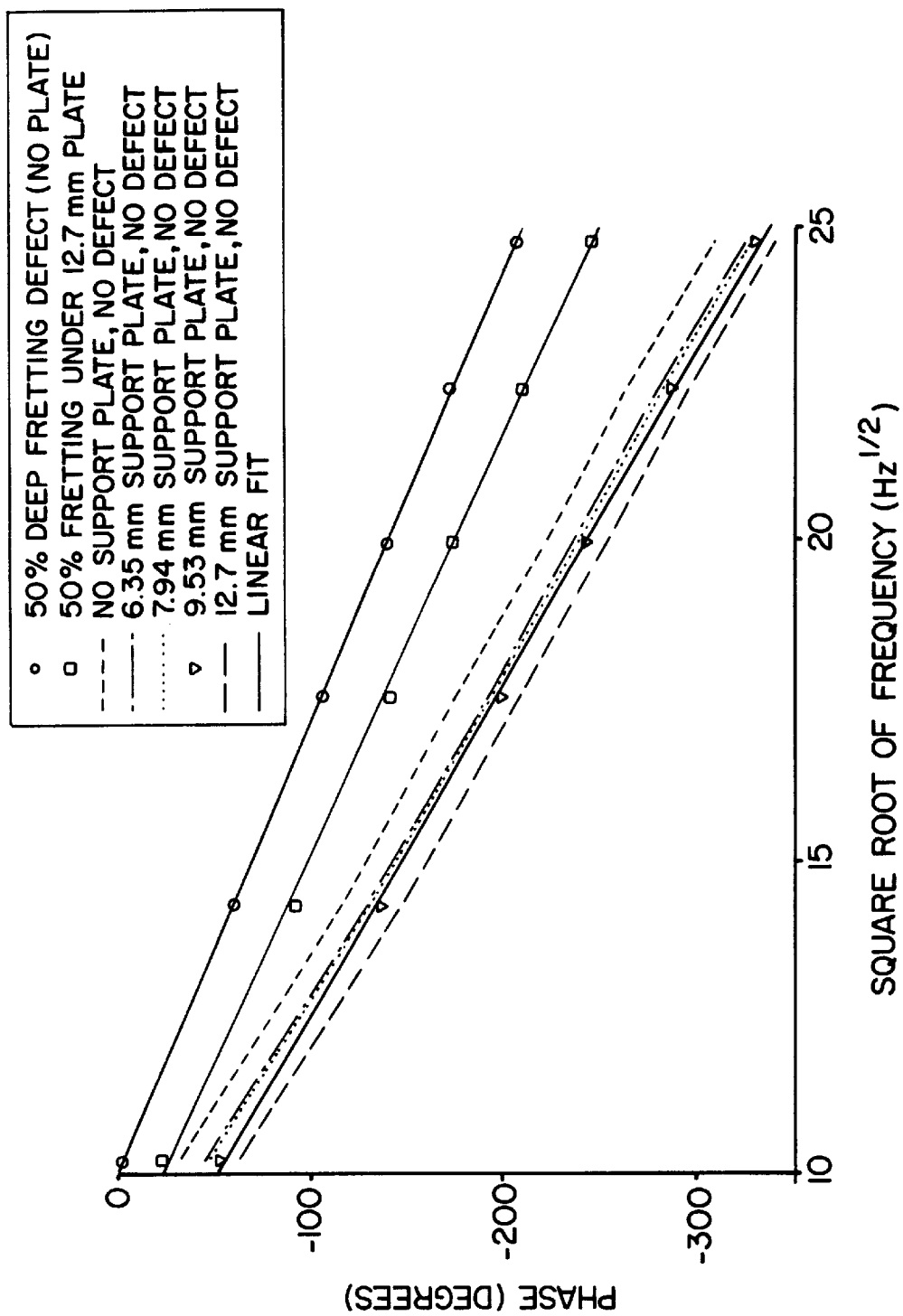
FIG. 7 is a graph illustrating influence of support plate thickness on the frequency dependence of T4 signals. Gap width between plate and pipe 0.2±0.05 mm. I=300 mA.

Fretting defects can be sized, by using T4 in combination with multi-frequency measurements. The phase-frequency curves for different support plates are compared in FIG. 7. The slopes in FIG. 7 are practically independent of the thickness of the plate, even if the thickness is reduced to zero. This indicates that the presence of support plates has essentially no effect on the slope of the phase-frequency curve. Note that the slope obtained for the 50% defect barely changes in the presence of the plate.

Figure 8:
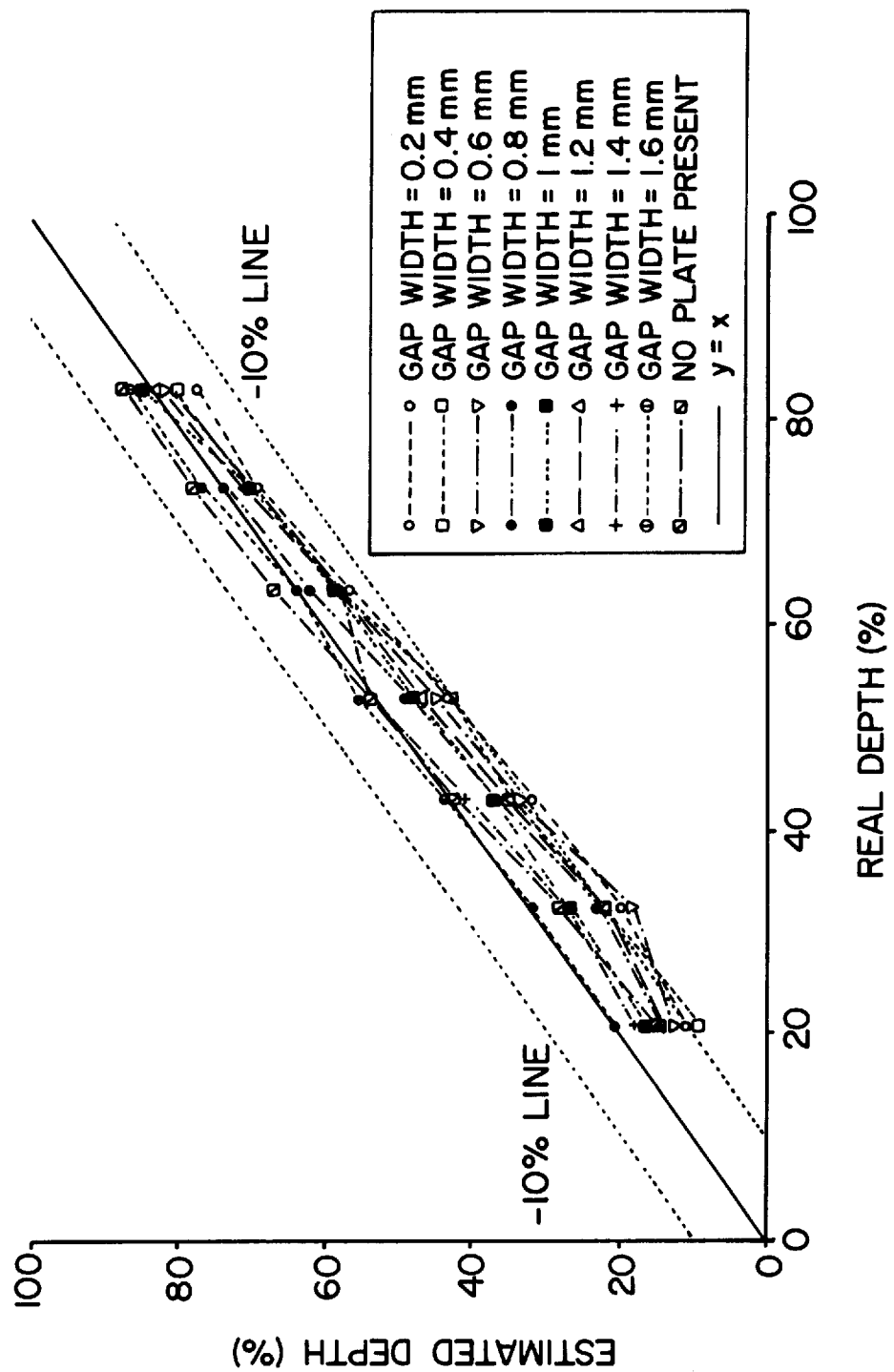
FIG. 8 is a graph illustrating sizing ability of T4. Full circumferential groove defects centered under 12.7 mm plates. I=300 mA, two pipes, detector in defect pipe. Various pipe plate gaps, as shown.

As described above, for defects without support plates, the slope can be used to estimate defect depth. Using the curves of FIG. 7 in combination with the skin depth equation, the depth of the 50% defect underneath the plate is estimated to be 43%. The depth estimation improves as the defects become deeper and the air gap becomes larger. The accuracy of the depth estimation depends on parameters such as defect depth, defect shape, support plate thickness and the gap width between pipe and plate. In general, an increased thickness of the support plate results in lower sizing accuracy, while a larger total air gap between pipe and plate improves the sizing accuracy. FIG. 8 shows the depth sizing performance for full circumferential grooves underneath the 12.7 mm thick plate. In general, the grooves are sized within 15% and the accuracy improves as the air volume between pipe and plate is enlarged.

Figure 9A:
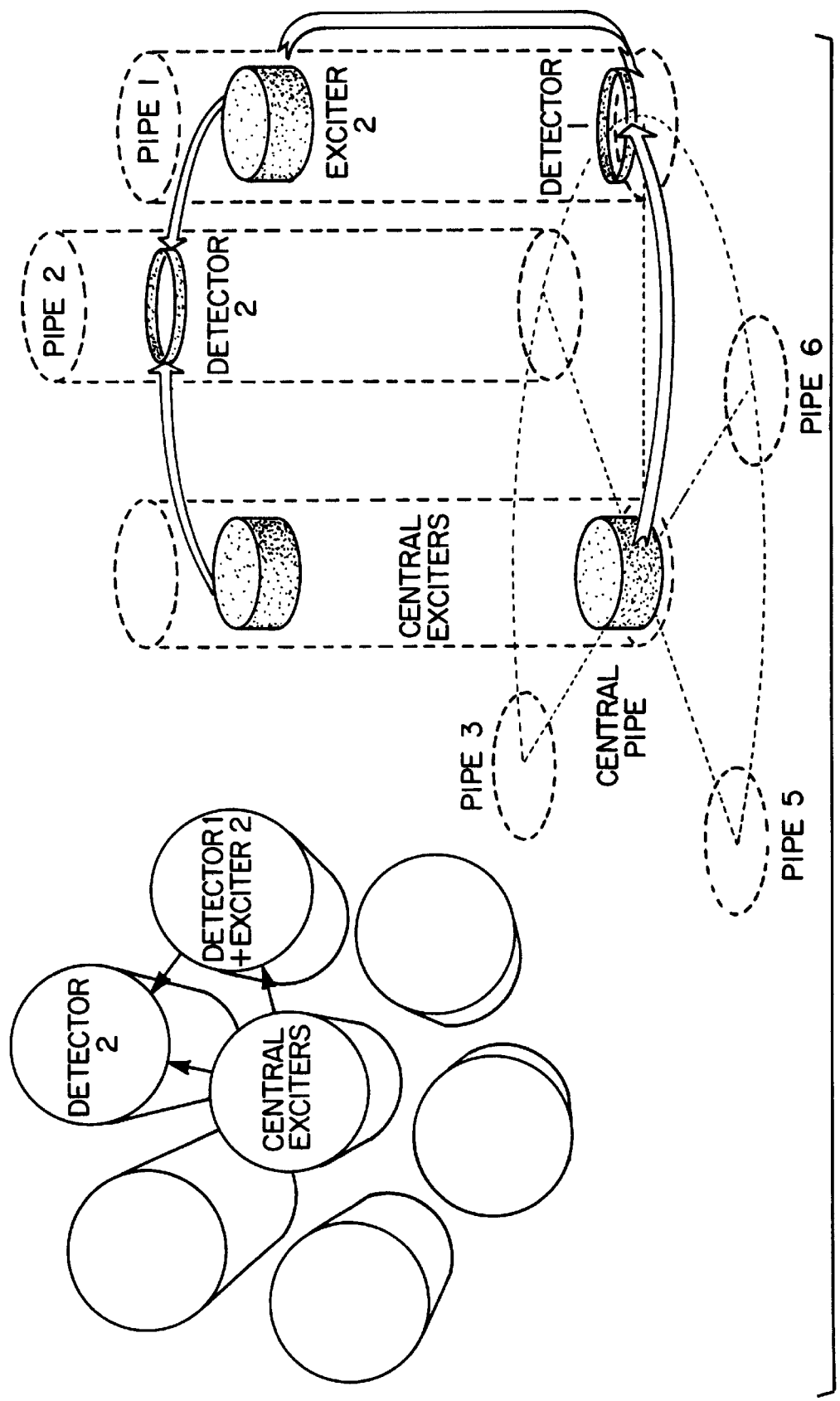
FIG. 9a is a sketch illustrating one T4 probe configuration in a bundle of pipes using two exciters.
Figure 9B:
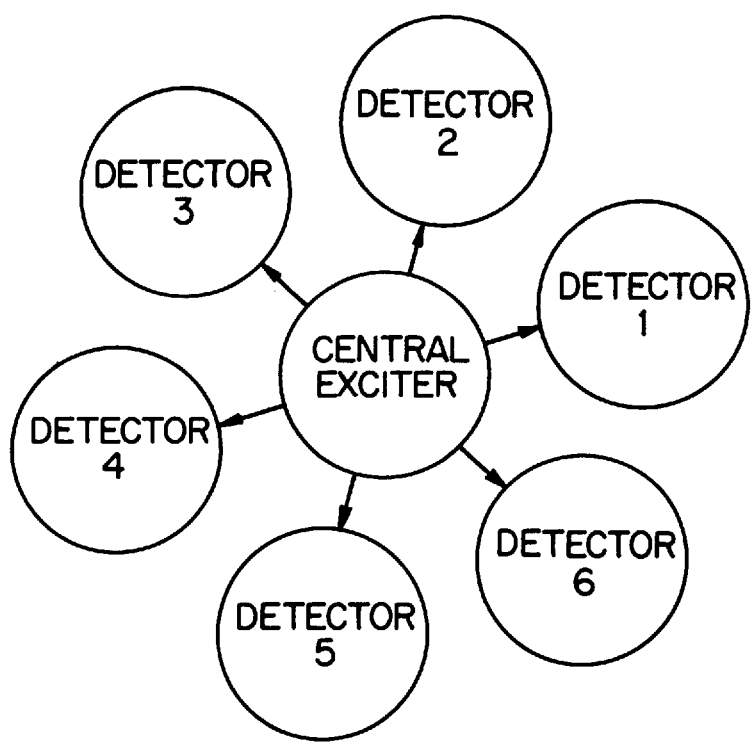
FIG. 9b is a sketch illustrating an alternative T4 probe configuration in a bundle of pipes using a set of circumferential detectors.

To supply information on several pipes simultaneously, some probe arrangements are indicated in FIG. 9. Configuration A, in FIG. 9, performs three T4 inspections simultaneously as well as a remote field inspection of pipe 1. Each T4 inspection provides information on the combined wall condition of the two pipes involved. The three T4 scans together, however, provide enough information to resolve each pipe condition separately. In case of uncertainty, the remote field scan can be used to provide additional information. A situation in which the additional remote field scan could be useful is the detection of small defects at the outside of the heat exchanger bundle.

An alternative probe arrangement is indicated in configuration B of FIG. 9. In this design, detectors are placed in as many as six directly neighbouring pipes. In case of a partial circumferential defect located in the central pipe, each of the 6 receivers will register a different defect signal. By combining the 6 individual responses, there is a better possibility of sizing and locating the defect around the circumference. The exciter coil in the central pipe can be used as the transmitter of a remote field probe, which will provide the information necessary to determine whether a defect is in the central tube or in one of its neighbours. Obviously, it is not very convenient for the operator to pull 7 probes at a time.

There are, of course, numerous other modifications possible, for example, the use of differential detectors, the use of a pulsed exciter current (transmission time will be the measure of wall thickness) and the inspection of pipes that are not direct neighbours.

Besides support plates, a number of other inspection problems exist for which tube-to-tube transmission may be employed. For example, finned tubes are used for the exchange of heat between an external gaseous medium and an internal liquid medium. The fins, which are good heat conductors and run externally around the pipe, improve heat transfer by increasing the contact surface between pipe and gas. At the same time, however, they make it practically impossible to inspect the pipes for external corrosion. In RFEC inspection, the energy coupling path runs axially from exciter to detector along the outside of the pipe. Clearly, the metallic fins interfere with the coupling path and make the tubes difficult to inspect. In T4 probes, however, the energy propogation/transmission path is oriented in the radial direction and therefore less affected by the fin-interference. If the fins are ferromagnetic, they will actually guide energy in the radial direction, partly compensating for the dissipation inside the fins. Initial measurements confirm that T4 can indeed by used to inspect finned tubes. Although the receiver signal is somewhat noisier than normal, small through wall defects in a finned pipe are detectable with the technique. The same defects were not detectable using ordinary RFEC.

Another problem area for conventional inspection techniques is the U-bend region of the heat exchanger. In this region, the pipes are bent over a 180° angle. The bends cause additional wall-thinning as well as an increased stress level in the pipe wall. The U-bend region is notorious for having a high failure rate, while being difficult to inspect. A T4 probe can be very short in the axial direction and can therefore handle sharp bends much better.

Figure 10:
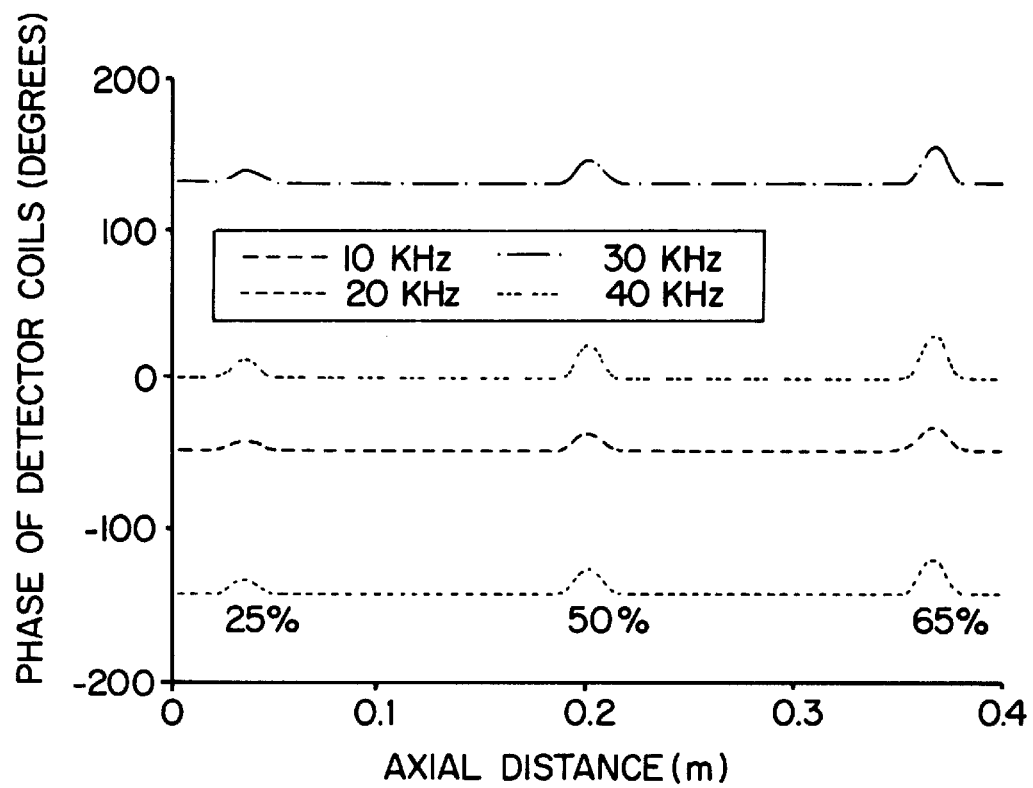
FIG. 10 is a graph illustrating the T4 response in two aluminium pipes. 24.5 mm full circumferential grooves in pipe with detector (5 mm long). Exciter current 300 mA.

The T4 technique is also applicable to the inspection of non-ferrous tubes, as seen in FIG. 10 which illustrates T4 in two aluminum pipes inspected in the KHz range. The detector was 5 mm long and placed in a pipe with full circumferential grooves, 24.5 mm long, and an exciter current of 300 mA was employed. As can be seen the signals were relatively noise free and fretting defects showed up well.

We claim:

1. A method for detecting flaws in at least one of a plurality of substantially parallel non-concentric stationary metal pipes comprising: passing an exciter coil along a first said metal pipe; passing a detector coil simultaneously along a second said metal pipe adjacent to said first metal pipe; energizing said exciter coil while in said first metal pipe with an AC current; detecting an AC magnetic field generated by said AC current with said detector coil in said second pipe and logging continuously varying output signals therefrom; and determining size, shape and location of defects in either said pipe from anomalies in said output signals.

2. A method as claimed in claim 1 wherein said metal pipes comprise a bundle of substantially parallel heat exchanger pipes.

3. A method as claimed in claim 2 wherein said pipes are selected from the group consisting of magnetic, non-magnetic and non-ferrous pipes.

4. A method as claimed in claim 3 wherein said pipes are finned pipes.

5. A method as claimed in claim 1, wherein a plurality of exciter coils are inserted into at least one of said plurality of metal pipes.

6. A method as claimed in claim 1 wherein a plurality of detector coils are inserted into at least one of said plurality of metal pipes.

7. A method as claimed in claim 5 wherein said plurality of exciter coils are inserted into a said metal pipe containing a detector coil.

8. A method as claimed in claim 6 wherein said plurality of detector coils are inserted into a said metal pipe containing an exciter coil.

9. An apparatus for detecting flaws in at least one of a plurality of substantially parallel non-concentric spaced metallic pipes comprising: an AC exciter coil adapted for passage along a first said metallic pipe; an AC magnetic field detector coil adapted for simultaneous passage along a second, adjacent, said metallic pipe; means to supply an AC current to said exciter coil so as to generate an AC magnetic field adjacent said detector coil; means to log output signals from said detector coil; and means to determine size, shape and location of said flaws in said second pipe from anomalies in said output signals.

10. An apparatus as claimed in claim 9 wherein said metallic pipes comprise a bundle of substantially parallel heat exchanger pipes.

11. An apparatus as claimed in claim 10 wherein said pipes are selected from the group consisting of magnetic, non-magnetic and non-ferrous pipes.

12. An apparatus as claimed in claim 11 wherein said pipes are finned pipes.

13. An apparatus as claimed in claim 9 including a plurality of AC exciter coils adapted for passage along one or a plurality of said metallic pipes.

14. An apparatus as claimed in claim 9 including a plurality of AC magnetic field detector coils adapted for passage along one or a plurality of said metallic pipes.

15. An apparatus as claimed in claim 13 wherein said plurality of AC exciter coils are adapted for passage along a said metallic pipe containing a said AC magnetic field detector coil.

16. An apparatus as claimed in claim 14 wherein said plurality of AC detector coils are adapted for passage along a said metallic pipe containing a said AC exciter coil.

* * * * *